(12) United States Patent
Al-Rasheed

(10) Patent No.: US 8,491,854 B2
(45) Date of Patent: Jul. 23, 2013

(54) SYSTEMS AND METHODS FOR CEREBROSPINAL FLUID COLLECTION

(75) Inventor: Abdullah Khalid Al-Rasheed, Riyadh (SA)

(73) Assignee: King Saud University, Riyadh (SA)

( * ) Notice: Subject to any disclaimer, the term of this patent is extended or adjusted under 35 U.S.C. 154(b) by 202 days.

(21) Appl. No.: 12/941,084

(22) Filed: Nov. 8, 2010

(65) Prior Publication Data

US 2012/0115181 A1    May 10, 2012

(51) Int. Cl.
*C12Q 1/04* (2006.01)

(52) U.S. Cl.
USPC ........... 422/547; 422/548; 422/549; 422/550; 422/558; 422/913; 422/914; 422/915; 422/916; 422/917; 422/918; 422/939; 422/949; 422/568; 422/569; 422/560; 222/568; 222/569; 222/570; 141/98; 141/319; 206/430; 604/6.15; 604/403; 210/513; 210/519; 210/521; 210/532.1; 210/511; 210/418; 210/419; 210/420; 210/421; 210/422; 210/423; 210/263; 210/264; 210/265; 73/1.73; 73/1.74

(58) Field of Classification Search
USPC ......... 422/547–550, 558, 913–918, 939–949, 422/568–570; 222/568–570; 141/98, 319; 206/430; 604/6.15, 403; 73/1.73, 1.74; 210/513, 210/519, 521, 532.1, 511, 418–423, 263–265
See application file for complete search history.

(56) References Cited

U.S. PATENT DOCUMENTS

| | | | |
|---|---|---|---|
| 5,396,899 A | | 3/1995 | Strittmatter |
| 5,772,607 A | | 6/1998 | Magram |
| 7,335,188 B2 | | 2/2008 | Graf |
| 2005/0038408 A1 | * | 2/2005 | von Segesser ................ 604/506 |
| 2005/0232813 A1 | * | 10/2005 | Karmali .......................... 422/58 |
| 2009/0204086 A1 | * | 8/2009 | Kizer et al. .................... 604/322 |

* cited by examiner

*Primary Examiner* — Jill Warden
*Assistant Examiner* — Shogo Sasaki
(74) *Attorney, Agent, or Firm* — Hart IP Law & Strategies

(57) ABSTRACT

A test tube insert includes a flange having a width greater than a width of a mouth of a larger test tube into which the insert is to be inserted. The flange defines a first central opening. An annulus extends integrally downward from the flange. The annulus includes a fenestrated wall and a floor defining a second central opening. A small test tube body, smaller than the larger test tube, extends integrally downward from the floor of the annulus with the second central opening forming a mouth of the small test tube body. The test tube insert is disposed in the mouth of the larger test tube. Fluid is transferred through the central opening and the fluid fills the small test tube body of the test tube insert and flows through the fenestrated wall once the small test tube body is full into the larger test tube.

6 Claims, 8 Drawing Sheets

700

SYSTEMS AND METHODS FOR CEREBROSPINAL FLUID COLLECTION

BACKGROUND

Cerebrospinal Fluid (CSF) analysis includes tests in clinical chemistry, hematology, microbiology, and serology. Usually three or four tubes of CSF are collected using a spinal tap (lumber puncture) procedure. The first tube is typically used for chemical and/or serological analysis and the last two tubes are used for hematology and microbiology tests. This reduces the chances of a falsely elevated red cell count caused by a traumatic spinal tap, wherein red blood cells may be in the CSF sample due to the spinal tap needle hitting a blood vessel while entering the skin or dura. The presence of red blood cells in a Cerebrospinal Fluid (CSF) sample also may be a sign of cerebrospinal bleeding. Thus, the red blood cell count in a CSF sample may be examined to determine if it returns to normal in samples taken later in the spinal tap procedure, as opposed to earlier. A ratio of the red blood cells to the white blood cells is also calculated to help with diagnosis. In addition, xanthcromia or clot formation of centrifuged CSF could indicate CSF bleed.

Differentiation between a traumatic tap and a hemorrhagic tap is important in the patient's management. If the tap is hemorrhagic, then a possibility of meningo-encephalitis or intracerebral bleed is present. Antiviral, antibiotic, or further brain imaging may be necessary for optimizing proper management. Arterial aneurism and arteriovenous malformation are other conditions that might result in a high red blood cell count in the CSF, which could require urgent neurosurgical intervention.

SUMMARY

The described systems and methods relate to cerebrospinal fluid collection. In one aspect, a test tube insert includes a flange having a width greater than a width of a mouth of a larger test tube into which the insert is to be inserted. The flange defines a first central opening. An annulus extends integrally downward from the flange. The annulus includes a fenestrated wall and a floor defining a second central opening. A small test tube body, smaller than the larger test tube, extends integrally downward from the floor of the annulus with the second central opening forming a mouth of the small test tube body.

In various CSF collection procedure embodiments, the test tube insert is disposed in the mouth of the larger test tube, with the flange spanning the mouth of the larger test tube. Fluid is transferred through the central opening in the flange; the fluid fills the small test tube body of the test tube insert, and then flows through the fenestrated wall extending between the flange and the small test tube body, once the small test tube body is full, into the larger test tube.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

In the Figures, the left-most digit of a component reference number identifies the particular Figure in which the component first appears.

DETAILED DESCRIPTION

Overview

The systems and methods described herein relate to collection of a first part and a last part of CSF during a spinal tap, which can play an important role in distinguishing a serious condition, such as subarachnoid hemorrhage, from a traumatic spinal tap. If red blood cell count is heterogeneous between the two, it is most likely a traumatic tap. If it is homogenous, it is most likely due to cerebrospinal hemorrhage secondary to encephalitis or a subarachnoid bleed. In daily practice, rarely is the first and last test tube of CSF from a spinal tap sent for a cell count, because it is tedious to add an extra tube to the CSF collection process and it will consume more CSF. The present systems and methods for CSF collection facilitate CSF collection from the beginning and the end of the CSF stream for comparative cell count.

In accordance with various implementations, the present procedures may add a small test tube (e.g., 0.5 cc), which can be fitted to the upper mouth of a first large CSF collection tube, during a spinal tap procedure. During the procedure, CSF will bathe the small tube in the center of the mouth of the large tube, as the larger tube is partially filled in a manner consistent with accepted CSF collection procedures. As a result, the small tube is filled with a sufficient CSF sample to test for red blood cells, without removing more CSF from the first tube sample than necessary. The rest of the CSF will collect in the bottom of the large first tube, per accepted clinical procedure. The two to three remaining large tubes are partially filled with CSF in the clinically accepted manner. Thereafter, in accordance with various implementations, the small tube is removed from the first larger tube and sent with the conventional blood cell count tube, typically the last (third or fourth) tube. Thus, a receiving hematology laboratory will have two tubes, the small first tube insert and the large last tube. This will facilitate the availability of two cell count readings, one from the first part of the CSF stream (the small tube) and the second from the last part of the CSF stream (the large last tube).

Particular examples discussed herein are discussed with respect to collection of CSF during a spinal tap, such as a lumbar puncture. However, the present systems and methods can be used in other fluid collection procedures where the differentiation of constituents of the fluid during the first part of collection from the constituents of the fluid later in the collection process is important.

An Exemplary System for CSF Collection

Figure 1:
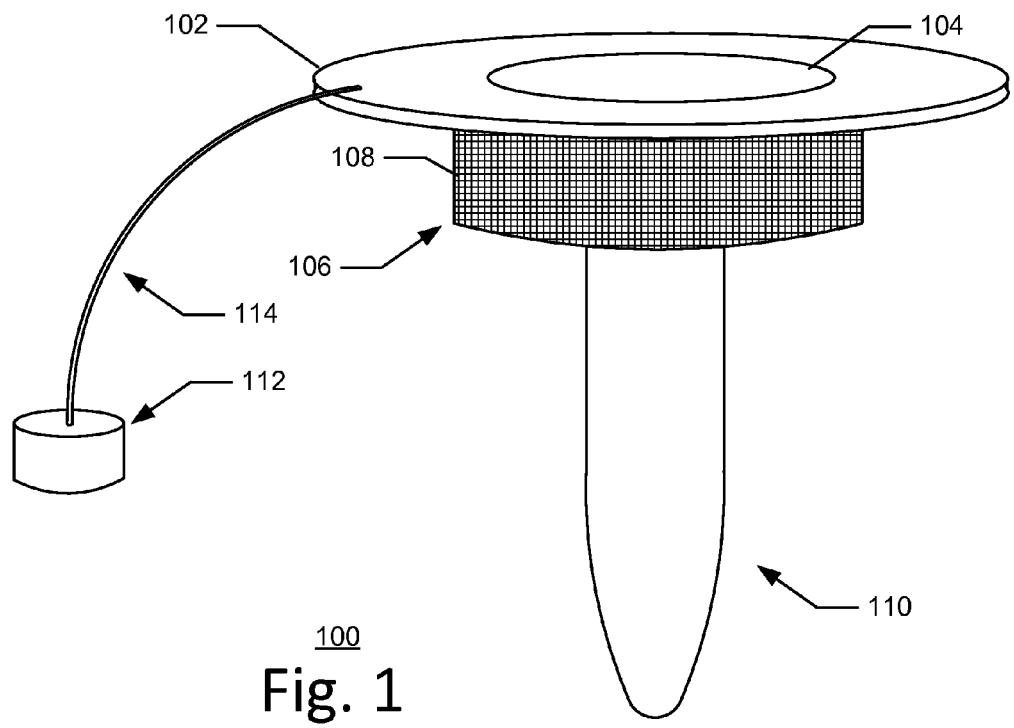
FIG. 1 is an enlarged perspective view of an example small test tube insert, according to one embodiment.

FIG. 1 is an enlarged perspective view of example small test tube insert 100, according to one embodiment. In accordance with the illustrated embodiment, test tube insert 100 includes flange portion 102 having a width greater than a width of a mouth of a larger test tube in which the insert is to be inserted. Flange portion 102 defines first central opening 104. In the illustrated embodiment, annulus portion 106 extends integrally downward from flange portion 102. Annulus portion 106 has fenestrated wall portion 108 and a floor portion defining a second central opening (not visible in the perspective of FIG. 1). Small test tube body portion 110 extends integrally downward from the floor portion of annulus portion 106. The second central opening forms a mouth of the small test tube body portion. In accordance with various implementations, small test tube body portion 110 is significantly smaller than the larger test tube to which insert 100 is to be fitted. Plug 112 is sized to plug the second central opening to seal small test tube body 110. Plug 112 may be flexibly linked to insert 100 using lanyard 114, or the like.

Figure 2:
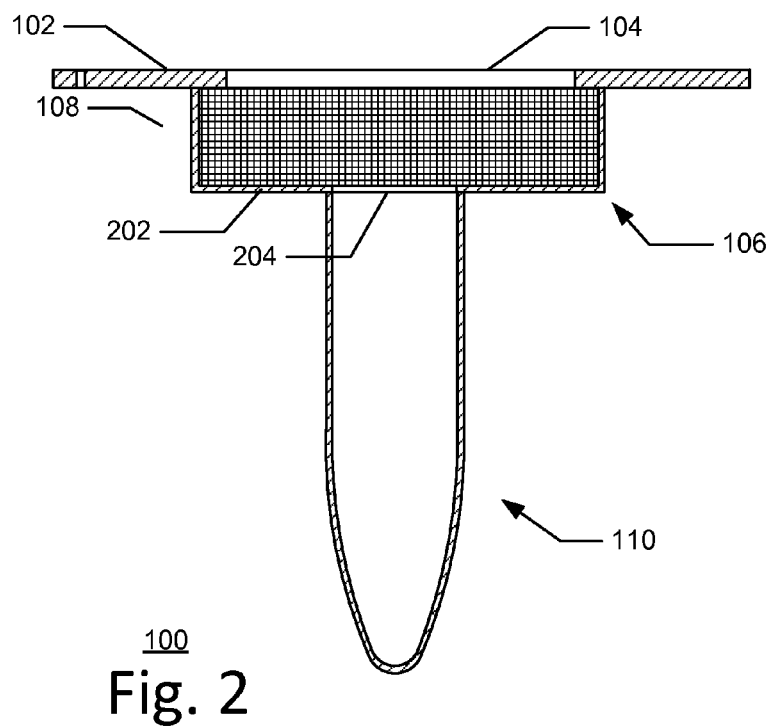
FIG. 2 is a fragmented, generally cross-sectional view of the example small test tube insert of FIG. 1, according to one embodiment.

FIG. 2 is a fragmented, generally cross-sectional view of example small test tube insert 100 of FIG. 1, according to one embodiment. Floor 202 of annulus 106 can be seen in FIG. 2, as can second central opening 204 defined in floor 202, which in turn defines the mouth of tube portion 110. As shown in FIG. 2, first central opening 104 may be concentric with and larger than second central opening 204. This may facilitate deployment of plug 112, as well as the capture of fluid by insert 100.

Figure 3:
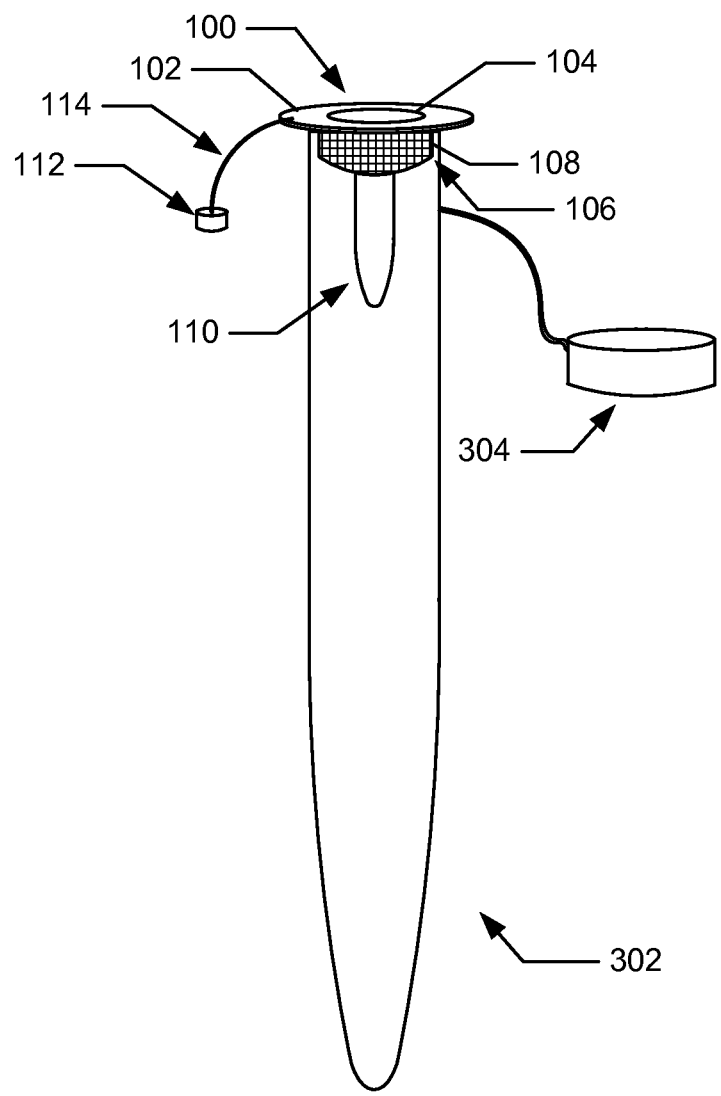
FIG. 3 shows the example small test tube insert of FIGS. 1 and 2 deployed in conjunction with a typical large test tube, according to one embodiment.

FIG. 3 shows example small test tube insert 100 of FIGS. 1 and 2 deployed in conjunction with typical large test tube 302, according to one embodiment. As discussed above, larger test tube 302 is a more-or-less conventional CSF collection test tube, which may be accompanied by cap 304. Typically, such a CSF collection test tube has an internal volume more than sufficient to accommodate a CSF sample of two to three milliliters. In contrast, small test tube body portion 110 has an internal volume of approximately one-half milliliter. This contrast in size is evident in FIG. 3.

Figure 4:
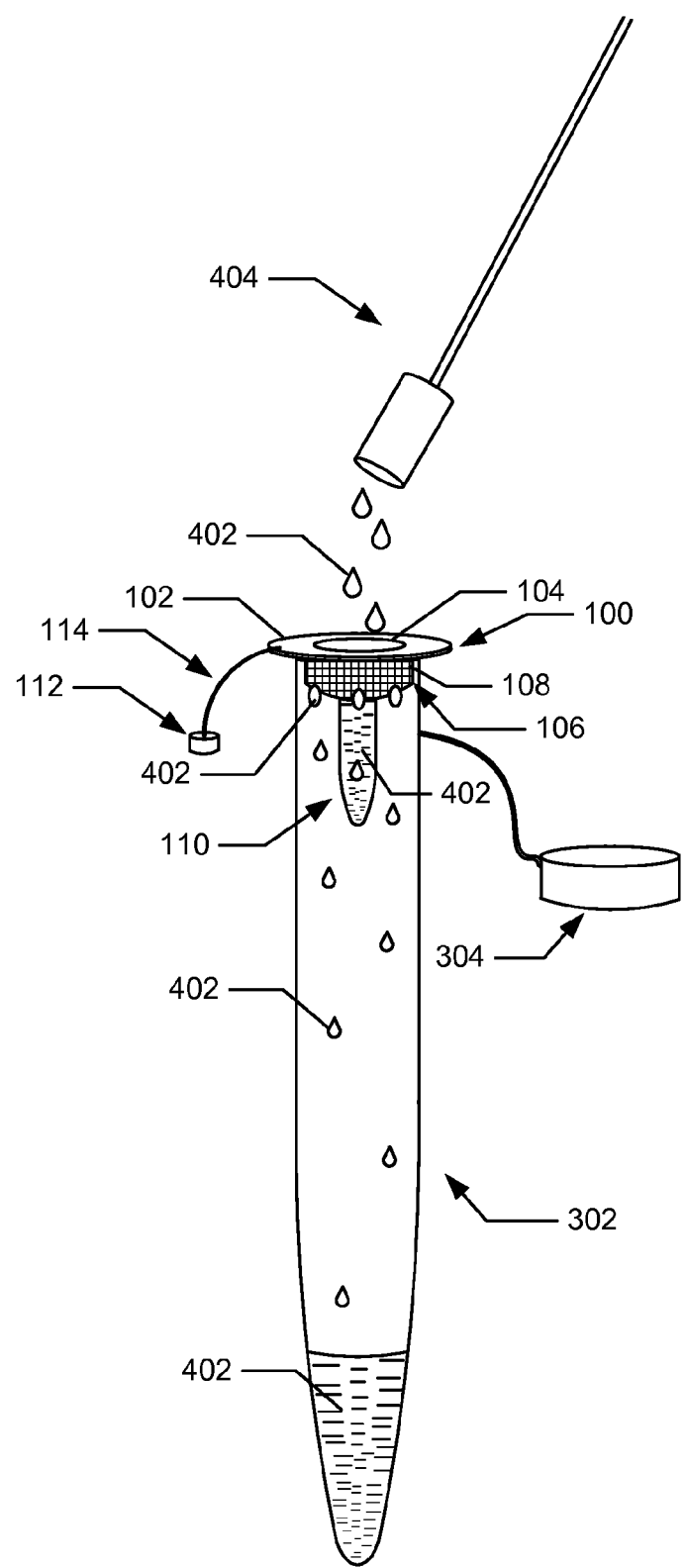
FIG. 4 is a diagrammatic illustration of collection of CSF using the combination of the example small test tube insert in conjunction with a typical large test tube shown in FIG. 3, according to one embodiment.

FIG. 4 is a diagrammatic illustration of collection of CSF 402 using the combination of example small test tube insert 100 in conjunction with typical large test tube 302 shown in FIG. 3, according to one embodiment. In FIG. 4, CSF 402 from spinal tap needle 404 is shown accumulated in test tube body portion 110 and flowing through fenestrated wall 108 of annulus portion 106 of insert 100 to collect in the end of large test tube 302.

Figure 5:
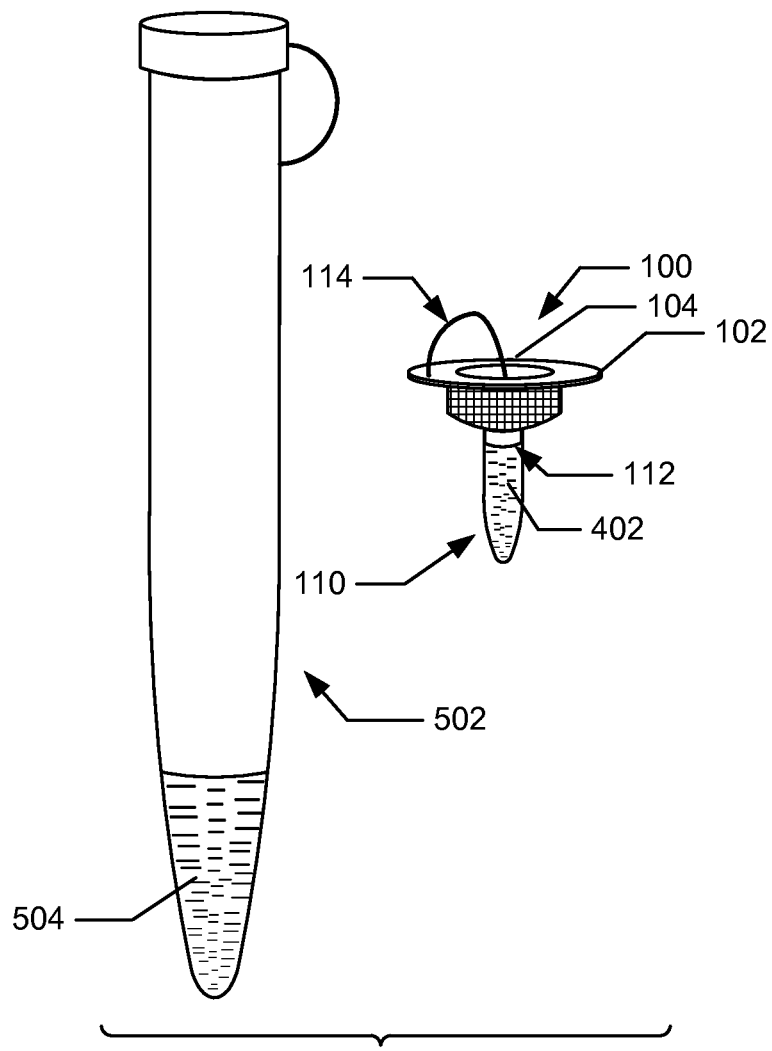
FIG. 5 shows the example small test tube insert of FIG. 1 plugged and a typical large test tube capped, each holding a CSF sample, according to one embodiment.

FIG. 5 shows example small test tube insert 100 of FIG. 1 plugged and typical large test tube 502 capped, each holding a CSF sample, according to one embodiment. FIG. 5 shows plug 112 deployed to plug small test tube body portion 110 of small test tube insert 100. In accordance with various embodiments, CSF 402 contained in small test tube body portion 110 of small test tube insert 100 is some of the first CSF collected. Meanwhile, CSF 504 contained in large test tube 502 is some of the last CSF collected during the procedure.

An Alternative Exemplary System for CSF Collection

Figure 6:
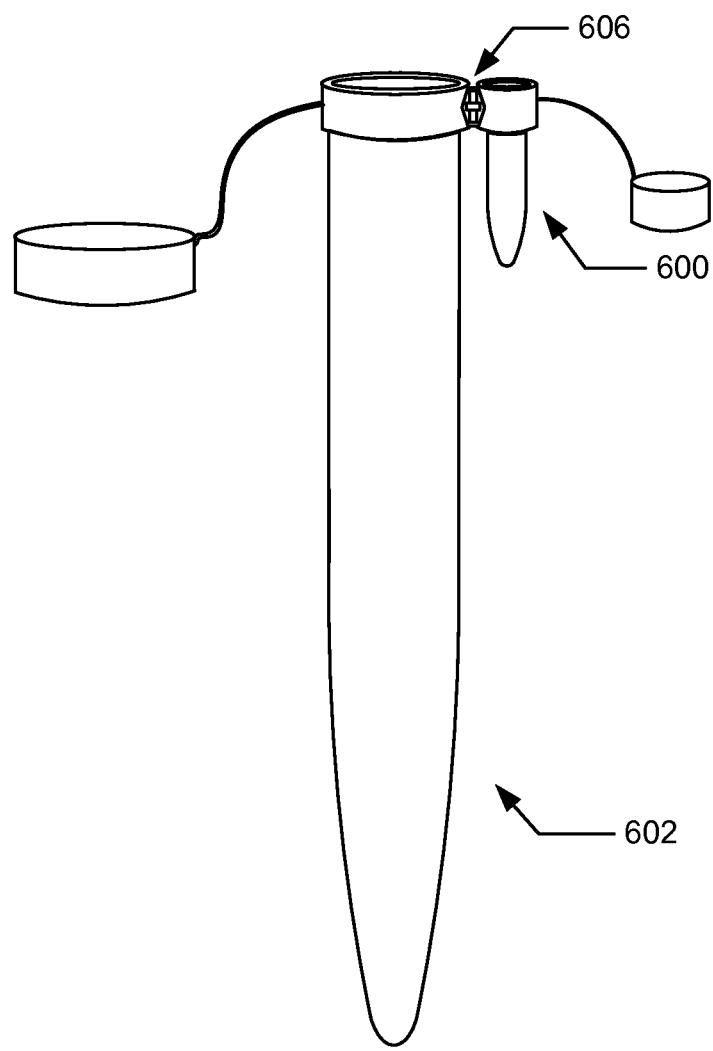
FIG. 6 shows an alternative embodiment of an example small test tube clipped to a typical large (first) test tube for collection of CSF, according to one embodiment.

FIG. 6 shows alternative embodiment example small test tube 600 clipped to typical large (first) test tube 602 for collection of CSF, according to one embodiment. In accordance with this implementation, relatively small test tube 600 accompanies first test tube 602 used for collecting cerebrospinal fluid, such as by relatively smaller tube 600 being clipped to first test tube 602, such as through the use of clip 606. Relatively smaller tube 600 may have an internal volume of approximately one-half milliliter, while more-or-less conventional CSF test tube 602 typically has a volume to more than accommodate a two to three milliliter sample of CSF. Relatively smaller tube 600 may be unclipped and accompany the typical test tube used to collect the last of the CSF sample for hematological testing. To facilitate this, tube 600 may be clipped to the test tube used to collect the last of the CSF sample in a manner similar to the manner in which it was clipped to first test tube 602.

An Exemplary Procedure for CSF Collection

Figure 7:
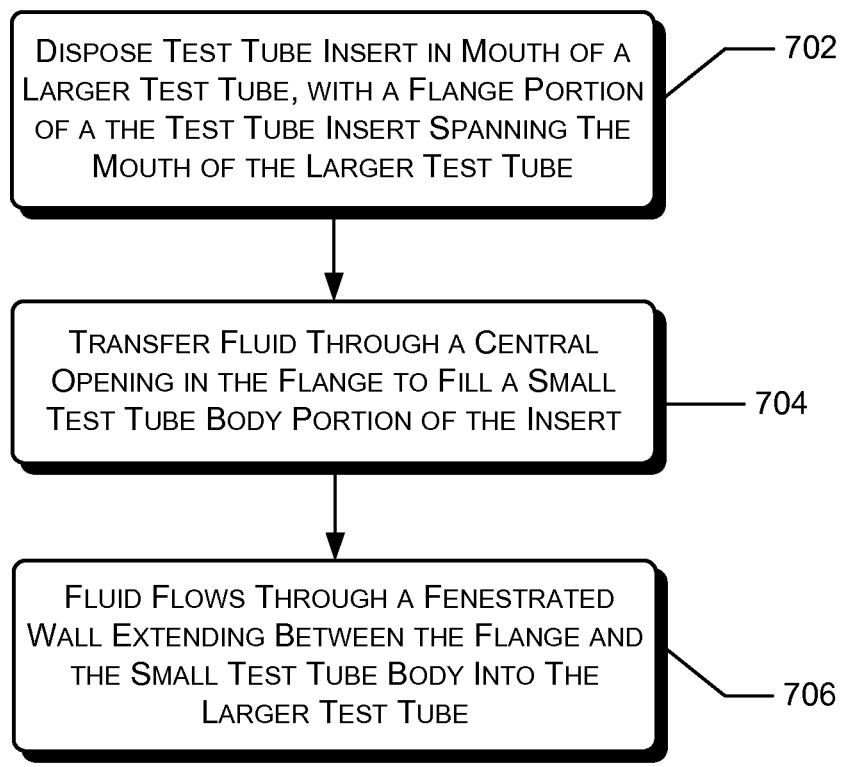
FIG. 7 shows an example procedure for collection of CSF, according to one embodiment.

FIG. 7 shows example procedure 700 for collection of CSF, according to one embodiment. Procedure 700 calls for disposing a test tube insert in a mouth of a larger test tube at 702, with a flange portion of the test tube insert spanning the mouth of the larger test tube. At 704, fluid such as CSF is transferred through a central opening in the flange, filling a small test tube body portion of the test tube insert. Once the small test tube body portion is full, fluid flows through a fenestrated wall extending between the flange portion and the small test tube body portion of the insert at 706 into the larger test tube, partially filling the larger test tube. Thereafter, the mouth of the small test tube body portion of the test tube insert may be plugged, and the test tube insert may be removed from the larger test tube, which may then be capped. Also, a plurality of subsequent larger test tubes may be filled with CSF. CSF thus collected, particularly the CSF in the test tube insert and a last of the plurality of subsequent larger test tubes filled, may be tested for the presence of red blood cells.

An Alternative Exemplary Procedure for CSF Collection

Figure 8:
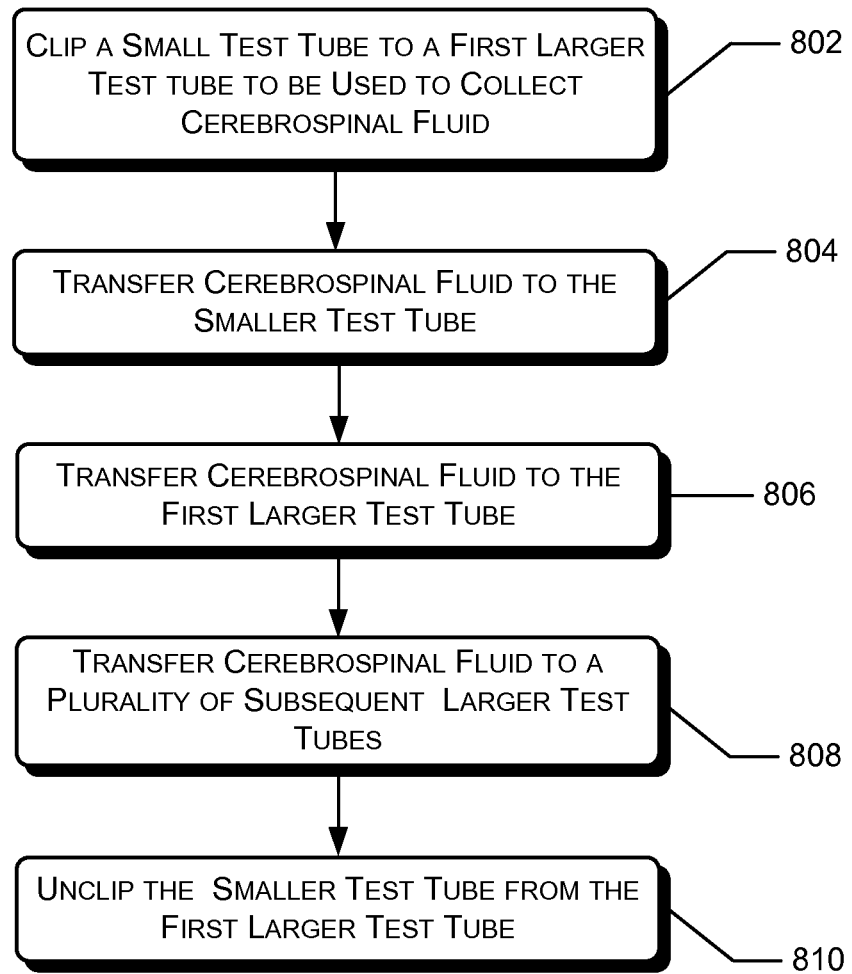
FIG. 8 shows an alternative embodiment of an example procedure for collection of CSF, according to one embodiment.

FIG. 8 shows alternative embodiment example procedure 800 for collection of CSF, according to one embodiment. At 802, a small test tube, relatively smaller with respect to a first test tube to be used to collect cerebrospinal fluid, is clipped to the first test tube. CSF is transferred to the small test tube at 804, then to the first test tube at 806, then to a plurality of subsequent test tubes at 808. At 810, the small test tube is unclipped from the first test tube and may accompany the last of the larger test tubes filled at 808 for hematological testing.

An Exemplary Procedure for Tap Differentiation

Figure 9:
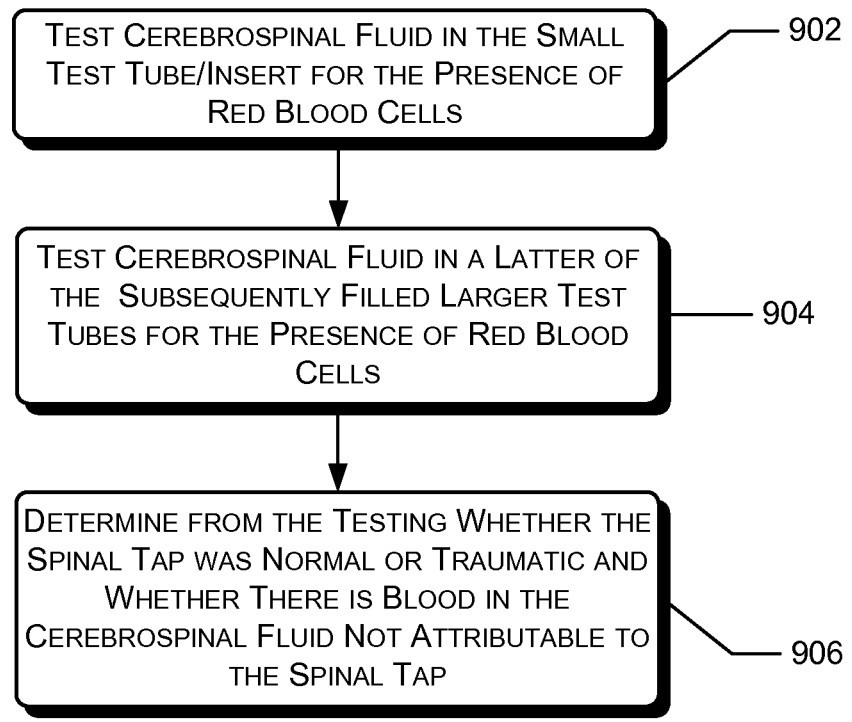
FIG. 9 shows an example procedure for differentiation of a clean spinal tap, traumatic spinal tap, and more serious conditions, according to one embodiment.

FIG. 9 shows example procedure 900 for differentiation of a clean spinal tap, traumatic spinal tap, and more serious conditions, according to one embodiment. In particular, following a collection as described above with respect to procedure 700 of FIG. 7 or procedure 800 of FIG. 8, the cerebrospinal fluid in the test tube insert or small test tube is tested for the presence of red blood cells at 902. At 904, a last of a plurality of larger subsequently filled test tubes are tested for the presence of red blood cells. A determination is then made at 906 from the test results from 904 whether a spinal tap employed to obtain the cerebrospinal fluid was normal or traumatic and whether there is blood in the cerebrospinal not attributable to the spinal tap. In 906, where a relatively low number of red blood cells are present in both the cerebrospinal fluid in the small test tube/insert and the last of the test tubes filled, the spinal tap is normal and no other condition exists that would cause an elevated blood cell count in the cerebrospinal fluid. At 906, where a large number red blood cells are present in the cerebrospinal fluid in the small test tube/insert, particularly relative to the last of the test tubes filled, the spinal tap is traumatic and no other condition exists that would cause an elevated blood cell count in the cerebrospinal fluid. At 906, where a large number of red blood cells are present in both the cerebrospinal fluid in the small test tube/insert and the last of the test tubes filled, a condition exists that would cause an elevated blood cell count in the cerebrospinal fluid, such as encephalitis or subarachnoid (or other central nervous system (CNS)) hemorrhage. The table below illustrates examples of such results.

| SAMPLE NUMBER | RED BLOOD CELL COUNT FROM SMALL TUBE | RED BLOOD CELL COUNT FROM LATTER TUBE | CONCLUSION |
|---|---|---|---|
| 1 | 3 | 0 | CLEAN TAP |
| 2 | 3462 | 179 | TRAUMATIC TAP |
| 3 | 292 | 278 | HOMOGENEOUS CSF - ENCEPHALITIS/CNS HEMORRHAGE |
| 4 | 655 | 34 | TRAUMATIC TAP |
| 5 | 193 | 201 | HOMOGENEOUS CSF - ENCEPHALITIS/CNS HEMORRHAGE |

CONCLUSION

Although systems and methods for CSF collection have been described in language specific to structural features and/or methodological operations or actions, it is understood that the implementations defined in the appended claims are not necessarily limited to the specific features or actions described. Rather, the specific features and operations of CSF collection are disclosed as exemplary forms of implementing the claimed subject matter.

The invention claimed is:

1. A test tube insert having a longitudinal axis from a first end to a second end, the test tube insert comprising:
    a flange portion having an upper surface and a lower surface in opposition to one another, a width of the lower surface in a direction perpendicular to the longitudinal axis, a height in a direction parallel to the longitudinal axis, the height between the upper surface and the lower surface being less than the width of the lower surface, and the flange defining a first central opening concentric with the longitudinal axis;
    an annulus portion extending integrally downward from the flange portion, the annulus portion comprising a fenestrated wall portion and a floor portion defining a second central opening; and
    a test tube body portion, the body portion extending integrally downward from the floor portion of the annulus portion, the second central opening concentric with the longitudinal axis, the second central opening forming a mouth of the small test tube body.

2. The test tube insert of claim 1, further comprising a plug sized to plug the second central opening to seal the test tube body portion.

3. The test tube insert of claim 2, further comprising a lanyard flexibly linking the plug to the flange portion.

4. The test tube insert of claim 1 wherein the first and second central openings are concentric.

5. The test tube insert of claim 1 wherein the first central opening is larger than the second central opening.

6. The test tube insert of claim 1 wherein the test tube body portion has an internal volume of approximately one-half milliliter.

* * * * *